(12) United States Patent
Mottate et al.

(10) Patent No.: US 6,358,043 B1
(45) Date of Patent: Mar. 19, 2002

(54) ORTHODONTIC APPLIANCE

(75) Inventors: Mikio Mottate; Masumi Kowata; Kiyoshi Shiga, all of Fukushima (JP)

(73) Assignee: Tomy Incorporated, Fukushima (JP)

( * ) Notice: Subject to any disclaimer, the term of this patent is extended or adjusted under 35 U.S.C. 154(b) by 0 days.

(21) Appl. No.: 09/618,810

(22) Filed: Jul. 18, 2000

(30) Foreign Application Priority Data

Jul. 19, 1999 (JP) ............................................ 11-204603
Jun. 20, 2000 (JP) ............................................ 12-184107

(51) Int. Cl.$^7$ ................................................. A61C 3/00
(52) U.S. Cl. ............................................. 433/8; 433/20
(58) Field of Search ................................. 433/8–17, 20

(56) References Cited

U.S. PATENT DOCUMENTS 5,176,951 A * 1/1993 Rudo ........................ 428/229
5,595,484 A   1/1997 Orikasa et al.

* cited by examiner

*Primary Examiner*—Nicholas D. Lucchesi
(74) *Attorney, Agent, or Firm*—Kenyon & Kenyon

(57) ABSTRACT

In an orthodontic appliance fit into the mouth, at least either one of an orthodontic bracket or an arch wire is composed of a composite resin. A reinforcing member is provided at a slot of the bracket and exposed to an inner wall surface of the slot. The reinforcing member is extended into tie wings which are formed as being extended toward the gingival side of the slot. and towards the occlusal side. The composite resin is a resin, e.g., a polymer alloy, in which two or more kinds of resin having contrary capacities, i.e., durability and adhesiveness, are blended. Further, a thermoplastic elastomer (TPE) is dispersed into a matrix resin to accomplish the strength and the solvent crack prevention, which are difficult to consist with each other. Dispersing TPE into the matrix resin is one kind of polymer alloying, and thus obtained resin is the composite resin.

22 Claims, 5 Drawing Sheets

29(39)

29(39)

ORTHODONTIC APPLIANCE

BACKGROUND OF THE INVENTION

1. Field of the Invention

The present invention relates to an orthodontic appliance, particularly relates to an orthodontic bracket made of plastic, and an archwire engaged to the bracket.

2. Description of the Related Art

So far, as the orthodontic bracket as an essential part of an orthodontic appliance, various materials such as metal, ceramics, plastics and the like have been employed. The orthodontic bracket has respective merits and demerits depending upon the material (raw material) of which it is made.

For example, the metal orthodontic bracket has a mechanical strength required in the orthodontic treatment, but has a demerit that the metal color will attract attention when a mouth is opened, giving an aesthetically undesirable impression.

The ceramic orthodontic bracket is aesthetically more excellent than the metal one, but has a demerit, for example, that the ceramics is materially harder than tooth enamel. This will often abrade occluded teeth and cause the archwire to be abraded as well. Further, since the ceramic orthodontic bracket is materially fragile, the bracket will be often cracked when it is applied with torque by an angular wire. Further, there may be a trouble that the tie wings supporting the ligature will be broken when the archwire is tied to the bracket.

Further, the ceramic orthodontic bracket has a high friction resistance compared with the metal one and will detract the slide property of archwire. Namely, the ceramic bracket tied onto the archwire will not smoothly slide along the archwire. This will prevent the effective movement of tooth and cause the orthodontic treatment to take more time.

The plastic orthodontic bracket is superior in moldability (processability), but has a demerit, for example, that aesthetic property will be lost due to the progress of discoloration and deterioration by chemical components and pigments contained in foods. Further, the plastic orthodontic bracket is inferior in mechanical strength compared with the metal one.

Especially the recent orthodontic bracket has been required to have a special aesthetic property in addition to the fundamental function required in orthodontics.

Therefore, the ceramic orthodontic bracket and plastic orthodontic bracket have come to be generally employed.

As to the ceramic orthodontic bracket and plastic one, the slot portion is, for example, contrived as is replaced by metal or other material to reinforce the slot portion and simultaneously decrease its friction resistance, and further the metal is provided as a core material (reinforcing member) inside of the bracket (U.S. Pat. No. 5,595,484).

Recently, resins of low water absorption have been developed, which will not be discolored, for example, by coffee having a relatively strong pigment.

Under these circumstances, demand for the plastic orthodontic bracket has been increased. The plastic orthodontic bracket is generally made of polycarbonate(PC) because the polycarbonate is superior in transparency, chemical stability, impact resistance, dimensional precision when molding in addition to non-poisonous property, thereby to heighten the adaptation for the orthodontic bracket.

Thus, the plastic orthodontic bracket is superior in aesthetic effect and has come to be generally employed.

However, the plastic orthodontic bracket has some problems remaining unsolved.

First of all, the problem is the solvent crack. Generally, the orthodontic bracket is directly adhered to a tooth by a dental adhesive. Therefore, in case the plastic bracket has an inner stress therein at the time of being molded (inner stress due to distortion generated when molding), the plastic bracket will often react to an organic solvent contained in the adhesive to produce the solvent crack at the bracket base and wings. As a result, the plastic bracket reduces the strength thereof to about $1/10$ of the standard strength rendering the plastic bracket to be useless.

In this respect, there has been an inconvenience that a specific adhesive, which will produce no possible problem, has to be selected in consideration of the compatibility between the plastic material for the orthodontic bracket and the solvent contained in the adhesive.

A second problem is lowered strength and aesthetic property due to the hydrolysis of synthetic resin.

Namely, it may be considered that the hydrolysis of polycarbonate is encouraged by the cut of ester coupling because carbonyl group is easily coupled to water molecule. Thus, the strength is reduced to a half of the original strength in about one year in the mouth of human body temperature. Further, the polycarbonate will easily be hydrolyzed if it has a high percentage of water contained before being molded. As results, it comes to invite the degradation of quality including bubbles created in the molded member, lack of surface luster, uneven fluidity, and lack of tensile strength and durability. Further, it is generally known that the plastics susceptible to hydrolysis will easily propagate microbes which produce the hydrolysis enzyme (enzyme for catalyzing hydrolysis) to accelerate the hydrolysis.

A third problem is adhesion strength.

Namely, it is preferable that the plastic orthodontic bracket is made of a resin of low water absorption which will produce no hydrolysis for a long period of time to maintain a desirable aesthetic property. However, the synthetic resin of low water absorption lacks the compatibility to the adhesive for obtaining sufficient adhesion strength to fix the resin to the tooth.

The plastic bracket having a reinforcing structure will be further specifically explained.

For example, the following plastic brackets having the reinforcing structure have been known. Namely, as disclosed in U.S. Pat. No. 4,299,569 and JP-A-9-98988, a metallic slot liner is provided in a mediodistal direction. As disclosed in U.S. Pat. Nos. 5,595,484, 5,813,852 and 5,597,302, a metal member having U-shaped cross section is insert-molded in the direction perpendicular to the slot.

In the metal slot liner structure and the metal insert structure, during the injection molding process, the liner and the insert member is disposed in an injection molding die prior to molding. Then, the resin encloses the liner and the insert member by the injection molding to form the plastic bracket. In this case, the resin for use is transparent or translucent and has high aesthetic property, such as polycarbonate, acryle, polyurethane and polyacetal, which are adhesive and water-resistant. However, in the molding process, during solidification of the resin by cooling, large residual stress occurs on the inside of the resin due to difference of expansion coefficients between the metallic liner/the insert member and the matrix resin.

Thus, in the structure in which the metallic liner and the insert member are integrally molded, comparatively large residual stress exists therein. Consequently, as described above, the plastic bracket senses to react with the adhesive solvent so as to cause the solvent crack when the bracket adheres to the tooth surface. Further, due to the existent residual stress, some kinds of resins accelerate the hydrolysis as described above. Thus, the tie wing or the like is broken before the generally required orthodontic treatment period (18 to 24 months).

Further, it has been generally performed that silane-coupling-treated inorganic filler, which is glass filler, is mixed to the matrix resin in an amount of 10 wt % to 50 wt %, to thereby enhance the mechanical strength. For example, as disclosed in U.S. Pat. Nos. 4,717,341 and 5,254,002, in the orthodontic appliance, the physical property and the durability of the bracket and the archwire are enhanced within such range as not to lower aesthetic property.

Glass filler is dispersed into the plastic bracket so as to enhance the cracking resistance property and the rigidity. Simultaneously, micro inner stress occurs. That is, a matrix resin having high inner stress exists around glass filler because of the difference of the thermal expansion coefficients between glass filler and the matrix resin when the resin is cooled and solidified at the time of injection molding. This micro inner stress (residual stress) is not actualized when the solvent of the orthodontic adhesive only temporally attached to the resin.

However, when the plastic bracket containing glass filler in the range of 10 wt % to 30 wt % was immersed in a test solution containing carbon tetrachloride and butanol in the ratio of 50:50 for one minute, the bracket was wholly whitened. This is because micro cracks are generated at portions having high inner stress around glass filler. Incidentally, the plastic bracket is not directly broken by these micro cracks. However, there is a problem that the durability is lowered by hydrolysis.

A metallic wire is mainly used as an orthodontic archwire. In order to enhance aesthetic property, a metallic wire as a core material is coated with fluorocarbon resin, whose color is close to white or tooth color. However, in this case, since the archwire is opaque, there is room for improvement regarding aesthetics.

In addition, there is a translucent archwire in which an optical fiber is used as a core material. However, since the orthodontic force is weak, its usage is restricted and it can not be suitable for practical use.

SUMMARY OF THE INVENTION

The objective of the present invention is to provide an orthodontic appliance capable of preventing the solvent crack in a bracket and maintaining a sufficient strength for a long period of time in the mouth. In the case of a bracket, the objective of the present invention is to provide the orthodontic appliance capable of obtaining sufficient adhesion strength.

In the case of an archwire, the objective of the present invention is to provide the orthodontic appliance that exhibits excellent capacities, e.g., optimal orthodontic force, aesthetic property and the like.

In this invention, orthodontic appliances that fit into the mouth as orthodontic means, at least an orthodontic bracket and/or an archwire comprise a component constructed by dispersing a thermoplastic elastomer in a matrix resin.

The above orthodontic appliance of the present invention is characterized in that:

the matrix resin is a polycarbonate resin and the thermoplastic elastomer is a styrene elastomer;

the content of the styrene elastomer is 0.5 wt % to 10 wt %;

the content of the styrene elastomer is 0.5 wt % to 2.0 wt %;

a particle size of the styrene elastomer is 0.1 μm to 10 μm;

a reinforcing member is provided at a slot of the bracket that is exposed to an inner wall surface of the slot so as to reinforce said inner wall surface;

the reinforcing member is extended and embedded into the tie wings which are formed as being extended towards the gingival side and occlusal side of the slot;

the reinforcing member has a hook core member provided to reinforce a hook of the bracket; and the matrix resin contains inorganic filler.

In the orthodontic appliance of the present invention, at least an orthodontic bracket and/or an archwire comprise an component constructed by dispersing a thermoplastic elastomer in a matrix resin. Accordingly, many voids formed by the elastomer can release strain which is a factor of stress concentration. Therefore, the orthodontic appliance can maintain the strength for use in the mouth for a long period of time.

In the orthodontic appliance of the present invention, the matrix resin is a polycarbonate resin and its thermoplastic elastomer is a styrene elastomer. Accordingly, myriad voids formed by the elastomer can further surely release strain which is a factor of stress concentration. Therefore, the orthodontic appliance can maintain the strength of use in the mouth for a long period of time.

In the orthodontic appliance of the present invention, the content of said styrene elastomer is 0.5 wt % to 10 wt %, and preferably, the content of said styrene elastomer is 0.5 wt % to 2.0 wt %. Accordingly, many voids formed by the elastomer can further surely release strain which is a factor of stress concentration. Therefore, the orthodontic appliance can favorably maintain the strength for in the mouth for a long period of time. Furthermore, if a particle size of said styrene elastomer is 0.1 μm to 10 μm, it is possible to obtain further stable strength.

In the orthodontic appliance of the present invention, reinforcing member is provided at a slot of the bracket. Said reinforcing member is exposed to an inner wall surface of the slot so as to reinforce said inner wall surface. Accordingly, the strength of the slot is enhanced and the orthodontic force can be surely applied to the slot for a long period of time.

In the orthodontic appliance of the present invention, the reinforcing member is extended and embedded into the tie wings which are formed as being extended towards the gingival side and occlusal side of the slot. Accordingly, it is possible to enhance the strength of the tie wings. Further, even if the tie wing is broken, it is possible to temporarily maintain ligature by the reinforcing member only.

In the orthodontic appliance of the present invention, the reinforcing member has a hook core member provided to reinforce a hook of the bracket. Namely, the reinforcing member is extended and embedded into the hook. Accordingly, the strength of the hook is enhanced and its application of the orthodontic force can be assured.

In the orthodontic appliance of the present invention, the matrix resin contains an inorganic filler. It is possible to not only enhance the resin strength but also adjust the transparency of the resin. Further, since both thermoplastic elastomer and glass filler exist in the synthetic resin, the solvent resistance of the orthodontic appliance is enhanced. Further, since the inner stress generated by glass filler is absorbed, it is possible to prevent micro cracks and suppress hydrolysis in the mouth.

An orthodontic bracket of the present invention having one end side surface fixed to a tooth and having the opposite end side formed with a slot which is designed to be engaged by an arch wire; comprises a composite resin having a first synthetic resin for providing a strength of the orthodontic bracket in the mouth and a second synthetic resin for providing an adhesion property thereof.

The above orthodontic bracket is characterized by:
the first synthetic resin that includes polyethylene-terephtalete and the second synthetic resin that includes polycarbonate which ranges 30 to 80 wt %;
said orthodontic bracket further comprises a bonding base area for providing a surface to be adhered to a tooth and a bracket member area which is continuous to the bonding base area and is formed with the slot and tie wings; wherein polycarbonate contained in the bonding base area is in the range of 60 to 100 wt %, and polyethylene-terephtalete contained in the bracket member area is 60 to 100 wt %; and
the synthetic resin contains inorganic filler therein.

The orthodontic bracket of the invention has one side surface to be fixed to a tooth and has the opposite side having a slot formed thereat so as to be engaged by an arch wire, comprises a composite resin including a first synthetic resin for maintaining a strength of the orthodontic bracket to be used in the mouth and a second synthetic resin for providing an adhesion property of the orthodontic bracket, the first synthetic resin being effective to maintain the orthodontic bracket to be used for a long period of time in the mouth, and the second synthetic resin being effective to secure an adhesion strength between the orthodontic bracket and the tooth.

According to the orthodontic bracket of the invention, polyethylene-terephthalete is used as the first synthetic resin and polycarbonate is used as the second synthetic resin, and polycarbonate ranges 30 to 80 wt % particularly for suitably maintaining the adhesion strength and the strength within mouth, and the rate of polyethylene-terephthalete (20 to 70 wt %) is used to remarkably reduce the residual stress at the time of molding, thereby to avoid the risk of the solvent crack.

The orthodontic bracket of the invention comprises a bonding base area providing thereat a surface to be adhered to a tooth and a bracket member area providing the slot and tie wings thereat which are continuous to the bonding area, and the bonding base area is formed with polycarbonate of 60 to 100 wt %, thereby to enable the polycarbonate of high adhesion strength to be used as a material for a portion to be adhered to remarkably increase the adhesion strength, and the bracket member area being is with polyethylene-terephthalete 60 to 100 wt %, thereby to enable the polyethylene-terephthalete to be used as a material for the bracket which is to be exposed in the mouth to remarkably increase the strength in the mouth.

An orthodontic bracket of the present invention having one end side surface fixed to a tooth and having the opposite end side formed with a slot which is designed to be engaged by an arch wire, comprises a reinforcing member provided in a bracket made of a synthetic resin so that a part of the reinforcing member or a base member fixed to the reinforcing member is exposed at a base surface which is positioned against the tooth.

Said orthodontic bracket is characterized by:
a rear surface of a bottom of the reinforce member or a rear surface of the base member is slightly recessed from the base surface;
the reinforce member is extended and embedded into the tie wings which are formed as being extended towards the gingival and occlusal sides of the slot;
the rear surface of the bottom of the reinforce member or the base member has a surface facing the tooth, the surface being rugged or meshy;
the synthetic resin is polyether-sulfone;
the synthetic resin is a composite resin; and
the synthetic resin contains inorganic filler therein.

According to the invention, the orthodontic bracket has a reinforcing member provided in the bracket made of synthetic resin, a part of the reinforcing member or a base member fixed to the reinforcing member is exposed at a base surface which is to be positioned against a tooth. Accordingly, the reinforcing member can be directly adhered to the tooth.

According to the orthodontic bracket of the invention, the reinforcing member has a bottom having a rear surface or a base member having a rear surface, and the rear surface of the reinforcing member or the rear surface of the base member is slightly recessed from the base surface. Therefore, the recessed portion may receive the adhesive therein.

According to the orthodontic bracket of the invention, the reinforcing member is extended and embedded into the tie wings. Accordingly, the strength of tie wings may be increased, and further the reinforcing member may temporarily maintain ligature in case the tie wings are broken.

According to the orthodontic bracket of the invention, the bottom of the reinforcing member or the base member has a surface which is to be against the tooth, and the surface is rugged or meshy. Therefore, the contact area of the surface may be increased or may produce an anchor effect to the adhesive.

According to the orthodontic bracket of the invention, the synthetic resin is polyether-sulfone which is harmless to human body and superior in durability.

According to the orthodontic bracket of the invention, the synthetic resin has inorganic filler, more particularly, glass filler contained therein. Therefore, it is possible to increase the strength of the synthetic resin, and further to adjust the transparency of the resin.

BRIEF DESCRIPTION OF THE DRAWINGS

FIG. 2A is a side view of the bracket in vertical section and FIG. 2B is a bottom view thereof;

PREFERRED EMBODIMENTS OF THE INVENTION

Preferred embodiments according to the present invention will be described in detail with reference to the accompanying drawings.

Figure 1A:
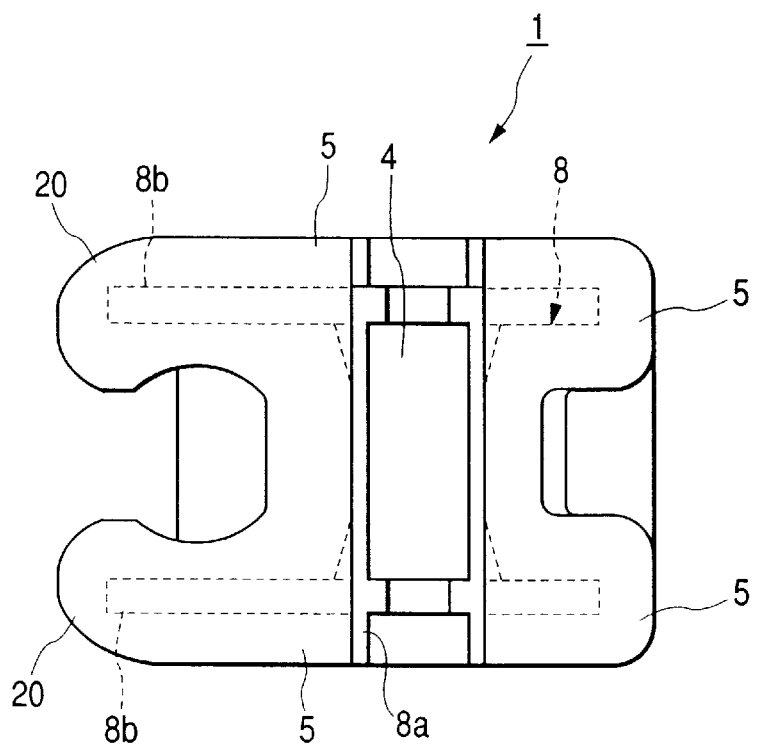
FIGS. 1A and 1B are schematical view and its side view, respectively, showing a first embodiment of an orthodontic bracket according to the present invention.
Figure 1B:
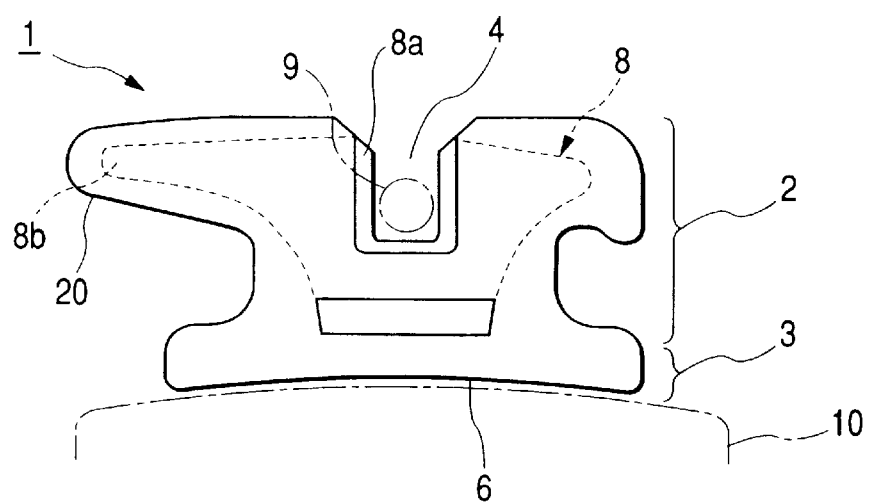

FIGS. 1A and 1B are schematic views showing a first embodiment of an orthodontic bracket according to the present invention. FIG. 1A is a plan view and FIG. 1B is a side view.

(First Embodiment)

As shown in FIGS. 1A and 1B, the orthodontic bracket 1 of the first embodiment is composed of a bonding base area 3 which has a bonding surface 6 slightly bent to be adhered to a tooth 10 and a bracket member area 2 which is continuous to the bonding base area 3. The bracket member area 2 has a slot 4 formed thereat as extending in the mesiodistal direction thereof for receiving an archwire 9 therein, and wings 5 which are formed as overhangs the gingival side and the occlusion side on both sides of the slot 4 respectively.

The bracket 1 is made of synthetic resin and has a reinforcing member 8 provided therein. The reinforcing member 8 is made of a metal or the like which has a high rigidity compared with the synthetic resin. The reinforcing member 8 may be made of a stainless steel plate, a metal injection molding product or the like.

The reinforcing member 8 exposed to the inner wall face of the slot 4 so that a slot exposing portion 8a for reinforcing the inner wall face is provided at the inner wall surface of the slot 4. According to the slot exposing portion 8a, the strength of the slot 4 is enhanced and the orthodontic force from the archwire 9 can be surely applied to the bracket body for a long period of time.

In the orthodontic appliance in this embodiment, the reinforcing member 8 is provided to extend to the inside of the tie wings 5. With this structure, the strength of the tie wing can be enhanced, and even if the tie wing 5 is broken, the ligature can be temporarily maintained by only the reinforcing member 8.

In this embodiment, a hook core portion 8b extended to the vicinity of the gingival end of the hook 20 is provided so that the reinforcing member 8 reinforces the hook 20 (structure in which one side of the tie wings 5 are largely projected) of the bracket 1. Thus, since the reinforcing member 8 is provided to be extend to the inside of the hook 20, the strength of the hook 20 can be enhanced.

The characteristic structure of this embodiment is that a synthetic resin composing the orthodontic bracket 1 is formed by dispersing an thermoplastic elastomer in its matrix resin. Accordingly, myriad voids formed by the elastomer can release strain which is a factor of stress concentration. Therefore, the orthodontic appliance can maintain the strength for use for long period of time. Further, since the adhesive capacity is good, it is possible to obtain a sufficient adhesive strength.

The strength of the bracket for use in the mouth is to be construed as follows; " . . . in view of the long period (normally 1 to 2 years) of the orthodontic treatment, the bracket is required to have a strength against the enzyme decomposition which may be caused by bacteria in the wet atmosphere of the mouth, against the hydrolysis which may be caused by the saliva and various drings, against the degradation of aesthetic property by a color stained and discoloration, against the damage of tie wing and deformation of slot which may be caused by the ligation force, against the damage of tie wings which may be caused by biting hard foods, against the deformation of slot which may be caused by a torque applied thereto by an angular wire, and against other adverse matters".

As to the orthodontic bracket 1 according to this embodiment, the first synthetic resin for use may be polyethylene-terephthalete, and the second polycarbonate that can be used. Further, it is preferable that polycarbonate ranges from 30 to 80 wt % in this composite resin.

Namely, if the ratio of polycarbonate is less than 30 wt %, the strength of the bracket is sufficient for use in the mouth, but it is out of practical use with respect to the adhesion strength. On the other hand, the ratio of polycarbonate is more than 80 wt %, the adhesion strength is sufficient, but it is problematical with respect to the strength of the bracket for use in the mouth.

As is generally known, the orthodontic bracket 1 thus provided has the bonding surface 6 at one end side thereof to be fixed to the tooth 10, and has the slot 4 at the opposite end side thereof to be engaged by the arch wire 9. The arch wire 9 is held there by a ligature.

In the present invention, the matrix resin is polycarbonate resin, and the thermoplastic elastomer is a styrene elastomer such as styrene-ethylene-butylene-styrene block copolymer (SEBS) or styrene-butadiene-styrene block copolymer (SBS).

The content of the styrene elastomer such as styrene-ethylene-butylene-styrene block copolymer (SEBS) or styrene-butadiene-styrene block copolymer (SBS) is in the range of 0.5 wt % to 10.0 wt %, preferably, 0.5 wt % to 2.0 wt %. Accordingly, it is possible to further surely release strain which is a factor of stress concentration. Therefore, the orthodontic appliance can favorably maintain the strength for use in the mouth for a long period of time. That is, as the added amount of the elastomer is increased, the void forming density is made large, therefore the toughness is enhanced by releasing strain. However, when the added amount of the elastomer is less than 0.5 wt %, there is little enhancement. On the other hand, when the added amount of the elastomer is more than 10.0 wt %, the toughness is decreased due to the lowered maximum load, but actually, good results can be obtained when the amount is less than 2.0 wt %.

Further, if the particle size of the styrene elastomer is in the range of 0.1 $\mu$m to 10 $\mu$m, it is possible to obtain stabler strength. At the time of injection molding of the resin in which the styrene elastomer (thermoplastic elastomer) is dispersed, the fluidity of the resin is enhanced so that the inner stress can be maintained at low level. Further, when the particle size is less than 0.1 $\mu$m, it is impossible to actualize the effect of myriad voids formed by the elastomer for releasing strain which is a factor of stress concentration. On the other hand, when the particle size is more than 10 $\mu$m, the mechanical strength is lowered.

The composite resin of polycarbonate/polyethylene-terephthalete (called as "PC/PET" hereinafter) may include for use, for example, a trade name of "DAIYA ALLOY P" of Mitsubishi Rayon Co., Ltd., a trade name of "HYPER LITE JP" of Kaneka Corp., a trade name of "CALIBER CR-3341" of Sumitomo Dow Ltd., a trade name of "IUPI-LON" of Mitsubishi Engineering-Plastics Corp. and the like.

The above described embodiment is directed to the orthodontic bracket. However, the present invention can also apply to the archwire 9. In this archwire 9, the thermoplastic elastomer is dispersed in the matrix resin in the range of 5% to 30%, so that the bending modulus is 10000 kg/cm$^2$ or more and the geometrical moment of inertia is 0.01 mm$^4$ or more. Accordingly, it is possible to use in Stage I and II in the orthodontic treatment.

With this structure, the archwire 9 has strong strength and is transparent or translucent, thereby becoming high aesthetic member.

In the above described orthodontic appliance the synthetic resin can contain glass filler. This structure can not only enhance the resin strength but also adjust the transparency.

In the orthodontic bracket of the invention thus structured, there can be no solvent crack due to the adhesive and no hydrolysis because of low water absorption while the durability is high in the mouth.

Further, the composite resin of PC/PET is excellent in fluidity at the time of molding and has little residual stress remained therein. Even if the residual stress remains at the time of molding, it is not sensitive to the solvent crack. Therefore, there is an advantage in production that the annealing which is otherwise required to eliminate the residual stress from PC may be skipped.

If the material is polyether-sulfone, the durability in the mouth, particularly against hydrolysis, is more excellent than polycarbonate, polysulfone and the like.

As to the color tone of the orthodontic bracket of the invention, since PC is used, the material is optimal for the plastic bracket of high aesthetic property because the material is characterized by non-crystalloid and transparency. On the other hand, the use of PC is problematical in deterioration of the resin due to solvent crack and hydrolysis. PET (a type of polyester), which is generally opaque crystal resin, may be alloyed with PC to be a translucent resin. Therefore, according to the invention, in case of, so called, a metal insert method wherein a metal reinforcing member is embedded within the bracket, the bracket may have a translucent or appropriate color to conceal the presence of reinforcing member.

The alloy of PC/PET in the market includes various grades, that is, substantially transparent, completely opaque, lower in transparency with glass filler added to increase the strength of bracket and the like, which may be optionally selected.

Further, PET includes a completely transparent amorphous one depending upon the grade as seen on PET bottles. The alloy of PET and PC may obtain a completely transparent alloy, though the technical explanation is omitted herein. In this case, it is preferable to make the alloy white. It is possible to cause the resin to have an inconspicuous translucent tone or a color like a tooth.

Although the PC/PET composite resin is used as a plastic material in the present invention, polyether-sulfone (that is not a composite resin) can also be used as a resin for the bracket. In this case, the thermoplastic elastomer is added to the polyether-sulfone in the range of 0.5 wt % to 10.0 wt %. This type of resin is more excellent in durability, particularly against hydrolysis, than polycarbonate and polysulfone, and has satisfactory adhesive capacity.

The thermoplastic elastomer is added to the matrix resin such as nylon, polyurethane and polypropylene in the range of 5 wt % to 30 wt %, so that fine particles of the thermoplastic elastomer will be exposed to the adhesive surface of the bracket. Accordingly, the adhesive is easily bonded to thereby enhance the adhesive strength.

In addition, the inorganic filler such as glass filler can be effectively added in the range of 10 wt % to 50 wt %.

The effects of the present invention were confirmed by the following test results of the orthodontic bracket of the present invention and comparative examples.

EXAMPLE 1

(1) Tests with Respect to the Solvent Crack, Hydrolysis and Strength of Tie Wing The orthodontic bracket as shown in FIGS. 1A and 1B was prepared, in which the housed reinforcing member extended into the tie wings. As composite resins, materials in which 0.5%, 1.0% and 2.0% of SEBS were mixed to polycarbonate resin lexan 144R (produced by GE plastic Corp.) were used to mold the plastic brackets housing the metal insert therein. For reference, 100% of lexan 144R containing no SEBS was also prepared.

PC/PET ("CALIBER CR-3341T produced by Sumitomo Dow Ltd.: polymer alloy of 70% of polycarbonate and 30% of polyethylene terephthalete) containing 1.0% of SEBS dispersed therein and PC/PET containing no SEBS were also prepared. The bonding base surface of each plastic bracket molded by using respective materials is coated with a primer or a monomer of each commercially available orthodontic adhesive. As time went by, the solvent crack was observed by a microscope.

The results are shown in Table 1. In Table 1;

"A" means that microcracks such as weld lines were observed mainly on the base surface, but it was judged that there was no problem.

"B" means that the number and the size of cracks on the base surface were conspicuous, but it was judged no problem for practical use.

"C" means that cracks spread to other areas in addition to the base area, which was judged useless.

Three specimens were used for each sampled batch.

TABLE 1

|  | U | V | W | X | Y | Z |
| --- | --- | --- | --- | --- | --- | --- |
| GE Lexan 144R | CCA | CCC | CCC | BCC | CCC | CCC |
| GE Lexan 144R + SEBS 0.5% | AAA | AAA | BBB | AAA | BBB | BBB |
| GE Lexan 144R + SEBS 1.0% | AAA | AAA | BBB | AAA | BBB | BBB |
| GE Lexan 144R + SEBS 2.0% | AAA | AAA | AAA | AAA | AAA | AAA |
| PC/PET(70:30) | AAA | AAB | AAA | AAA | BBC | CCC |
| PC/PET(70:30) + SEBS 1.0% | AAA | AAA | AAA | AAA | AAA | BAB |

U: GAC (Elan Plastic Primer)
V: Sun Medical (Super Bond Monomer)
W: GAC (Ortholock Primer)
X: Reliance (Plastic Conditioner)
Y: ORMCO (Spirit No Mix Primer)
Z: Sankin Industries (Suncure Primer)

According to the above results, it was found out that the larger the amount of SEBS was used, the more possible it is to prevent cracks from occurring. Depending on the solvent components of the primer and monomer of the adhesives, the stresses where cracks occur are different from each other. However, in any case, SEBS prevents cracks from spreading, and respective samples containing SEBS were determined to be suitable for practical use.

In PC/PET which is comparatively durable against the solvent crack, 1.0% of SEBS exhibits the effect to suppress cracks. According to this result, it was found out that also in the polymer alloy such as PC/PET, when small particles (0.1–10 μm) of the thermoplastic elastomer such as SEBS were dispersed, the inner stress was absorbed and, as a result, the solvent crack were hard to occur.

Next, the ratio of carbon tetrachrolide and butanol were changed in order to quantitatively comprehend to what extent the inner stress due to the metal insert could be decreased by mixing SEBS. This method is usually carried out to measure the inner stress of plastic molding products.

The same samples were immersed in the solution of carbon tetrachrolide and butanol at room temperature for one minute. The results are shown in Table 2.

TABLE 2

| Material for product | Mixing ratio of carbon tetrachrolide and butanol | Occurrence condition of cracks |
|---|---|---|
| GE Lexan 144R 100% | 0:100 | A: No cracks |
|  | 25:75 | B: Micro cracks generated on base surface |
|  | 50:50 | C: Cracks spread to whole area |
| GE Lexan 144R + 0.5% of SEBS | 0:100 | A: No cracks |
|  | 25:75 | A: No cracks |
|  | 50:50 | B: Micro cracks generated on base surface |
|  | 75:25 | C: Cracks spread to whole area |

As shown on Table 2, the materials containing only 0.5% of SEBS decreases the inner stress to suppress the occurrence of the solvent crack (cracks induced by solvent).

No crack would keep water and oil from seeping into the bracket, which accordingly yield increased durability and make it less susceptible to coloring or discoloration.

Further, it was confirmed by the tests that a minute amount of SEBS did not affect the adhesion capacity of the plastic bracket.

Moreover, the plastic bracket made of polycarbonate containing 20 wt % of glass filler, to which 2.0 wt % of SEBS was mixed, was prepared. It was immersed in the test solution, in which the content ratio of carbon tetrachrolide and butanol is 50:50, at room temperature for one minute. As a result, whitening phenomenon was not observed.

Accordingly, it was found out that mixing SEBS not only enhances the solvent resistance of the orthodontic appliance containing glass filler but also absorbs the inner stress generated by glass filler. Therefore, it prevents microcracks, suppress hydrolysis, and enhance durability.

(Second Embodiment)

Figure 1C:
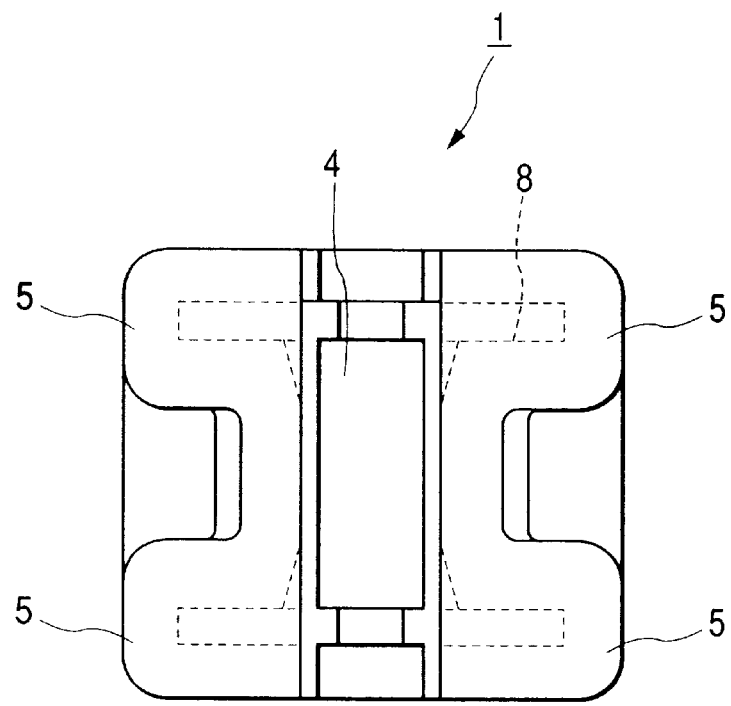
FIGS. 1C and 1D are schematical view and its side view, respectively, showing a second and third embodiments of an orthodontic bracket of the present invention.
Figure 1D:
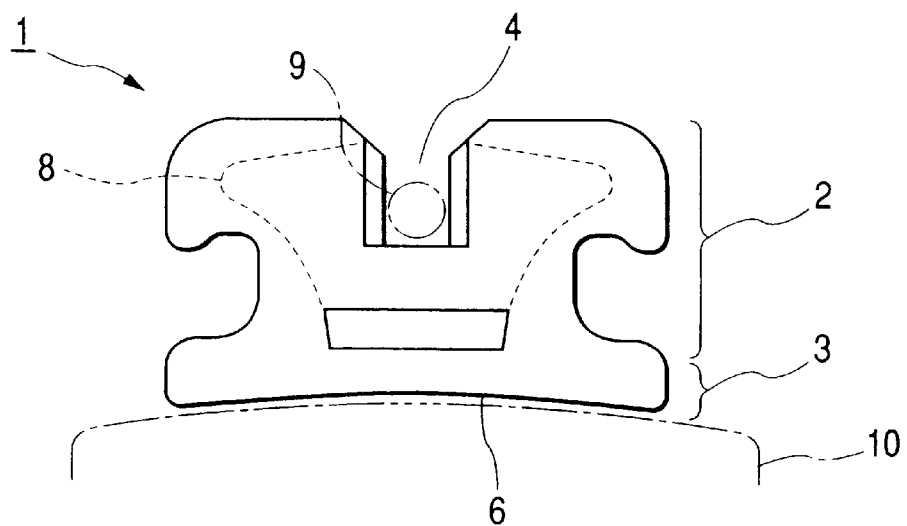

As shown in FIGS. 1C and 1D, an orthodontic bracket 1 according to the second embodiment is composed of a bonding base area 3 which has a bonding surface 6 slightly bent to be adhered to a tooth 10 and a bracket member area 2 which is continuous to the bonding base area 3. The bracket member area 2 has a slot 4 and tie wings 5. The slot 4 is formed on the bracket member area 2 as extending in the mesiodistal direction of the bracket for receiving an archwire 9 therein. The tie wings 5 which are formed as overhangs the gingival side and the occlusal side on both sides of the slot 4 respectively.

The bracket 1 is made of synthetic resin and has a reinforcing member 8 provided therein. The reinforcing member 8 is made of a metal or the like which has a high rigidity compared with the synthetic resin. The reinforcing member 8 may be made of a stainless steel sheet, a metal injection molding product or the like.

The feature of this embodiment is that the orthodontic bracket 1 is composed of a composite resin having a first synthetic resin for providing a strength of the bracket for use in the mouth and a second synthetic resin for providing an adhesion property. Such a composite resin prevents the solvent crack which may be caused at the time of adhesion while maintaining a sufficient strength for a long period of time with the adhesion strength being secured.

The strength of the bracket for use in the mouth is to be construed as follows; "in view of the long period (normally 1 to 2 years) of the orthodontic treatment, the bracket is required to have a strength against the enzyme decomposition which may be caused by bacteria in the humid atmosphere of the mouth, against the hydrolysis which may be caused by the saliva and various drinks, against the degradation of aesthetic property by a color stained and discoloration, against the damage of tie wings and deformation of slot which may be caused by the tying force, against the damage of tie wings which may be caused by biting hard foods, against the deformation of slot which may be caused by a torque applied thereto by an angular wire, and against other adverse matters".

As to the orthodontic bracket 1 according to this embodiment, the first synthetic resin may be polyethylene-terephthalete and the second synthetic resin may be polycarbonate. Further, it is preferable that polycarbonate ranges from 30 to 80 wt % in the composite resin.

Namely, if the amount of polycarbonate is less than 30 wt %, the strength of the bracket is sufficient for use in the mouth, but the bracket is out of practical use with respect to the adhesion strength. On the other hand, if it is more than 80 wt %, the adhesion strength is sufficient, but the bracket is problematical with respect to the strength of the bracket for use in the mouth.

As is generally known, the orthodontic bracket 1 thus provided has the bonding surface 6 at one end side thereof to be fixed to the tooth 10, and has the slot 4 at the opposite end side thereof to be engaged by the archwire 9. The archwire 9 is held there by a ligature (not shown).

The composite resin of polycarbonate/polyethylene-terephthalete (called as "PC/PET" hereinafter) may include for use, for example, a trade name of "DAIYA ALLOY P" of Mitsubishi Rayon Co., Ltd., a trade name of "HYPER LITE JP" of Kaneka Corp., a trade name of "CALIBER CR-3341" of Sumitomo Dow Ltd., a trade name of "IUPI-LON" of Mitsubishi Engineering-Plastics Corp. and the like.

(Third Embodiment)

In the third embodiment, the orthodontic bracket 1 shown in FIGS. 1C and 1D as similar to the second embodiment is used. The third embodiment will be described in reference to FIGS. 1C and 1D.

The feature of the third embodiment is that the bonding base area 3 contains 60 to 100 wt % of polycarbonate (PC), while the bracket member area 2 contains 60 to 100 wt % of polyethylene terephthalete (PET).

Thus, with the orthodontic bracket 1 having the bonding base area 3 of 60 to 100 wt % of PC, the bonding base area 3, that is, the bonding base surface 6 is formed with a resin of rich PC. As a result, the bonding base surface 6 has a high adhesion property.

Incidentally, when the amount of PC was 60 wt % or less, the property of PC was not sufficiently exhibited.

On the other hand, with the orthodontic bracket 1 having the bracket member area 2 of 60 to 100 wt % of PET, the bracket member area 2 is of rich PET. Incidentally, when the amount of PET was 60 wt % or less, the property of PET was not sufficiently exhibited.

The peripheral edges of the bonding base surface 6 and bonding base area 3, which are substantially formed with PC, are sealed with an adhesive. Therefore polycarbonate is not exposed in the mouth. This will compensate the weak point of PC (PC relatively lacks the strength for use in the mouth). As a result, the orthodontic bracket 1 adhered to the tooth 10 may exhibit the function of PET, that is the prominent strength for use in the mouth.

(Fourth Embodiment)

Figure 2B:
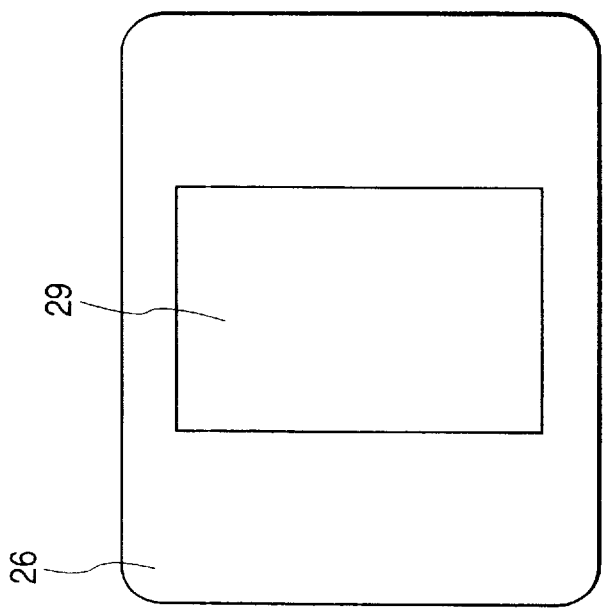
FIGS. 2A and 2B are schematical views showing a fourth embodiment of an orthodontic bracket according to the present invention.
Figure 2A:
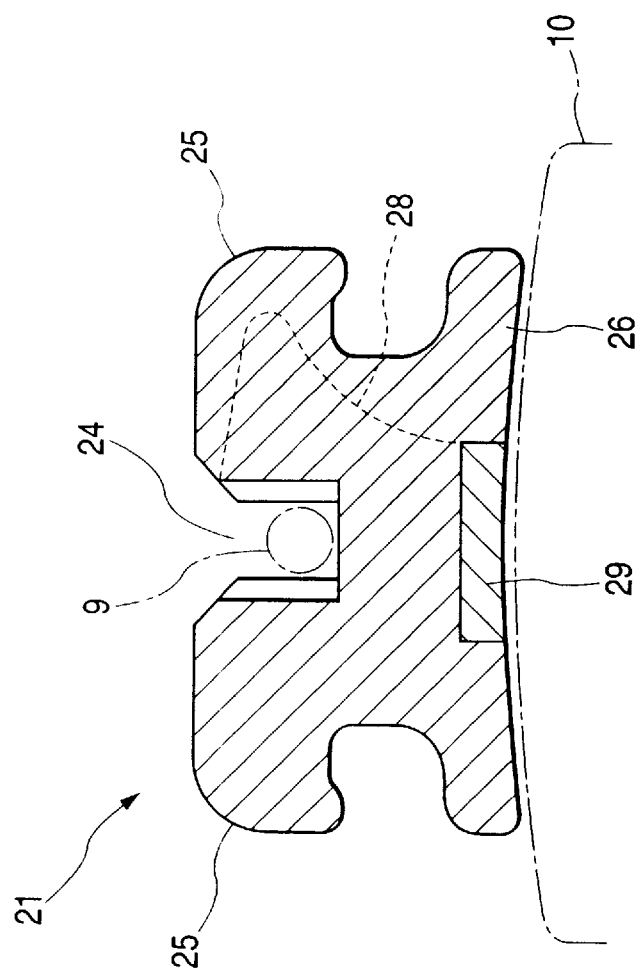

The orthodontic bracket 21 according to the fourth embodiment as shown in FIGS. 2A and 2B is formed in the same manner as the embodiment shown in FIGS. 1C and 1D. Namely, the orthodontic bracket 21 has one end surface fixed to the tooth 10 and has the opposite end side formed with a slot 24 extended between a pair of tie wings 25 for receiving the archwire 9 therein.

The orthodontic bracket 21 is made of a synthetic resin and has a reinforcing member 28 provided therein. The reinforcing member 28 has a bottom rear surface 29 exposed in the same plane with a bracket base surface 26 so as to form a part of the bracket base surface 26.

Thus, with the reinforcing member 28 having the part thereof (bottom rear surface 29) exposed at the bracket base surface 26, the bottom rear surface 29 compensates the adhesion strength. Further, with the reinforcing member 28 being directly adhered to the tooth 10, the adhesion of the orthodontic bracket 21 is so consolidated and assured.

(Fifth Embodiment)

Figure 3:
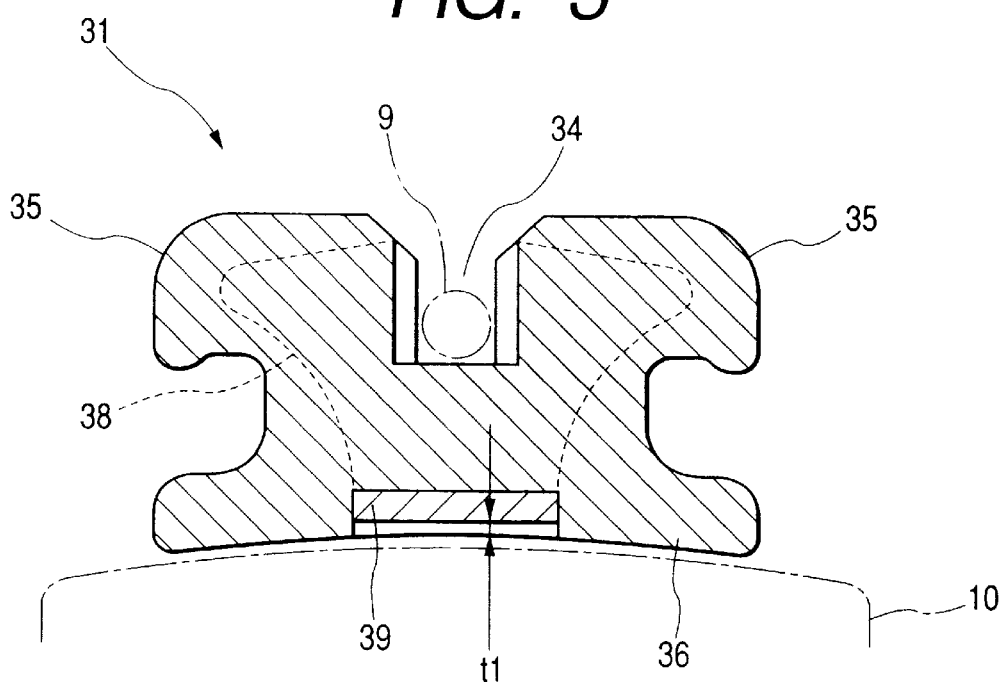
FIG. 3 is a diagrammatical view of a fifth embodiment of an orthodontic bracket according to the present invention shown in vertical section.

The orthodontic bracket 31 according to the fifth embodiment as shown in FIG. 3 is formed in the same manner as the embodiment shown in FIGS. 2A and 2B. Namely, the orthodontic bracket 31 has one end surface fixed to the tooth 10 and has the opposite end side formed with a slot 34 extended between a pair of tie wings 35 for receiving the archwire 9 therein.

The orthodontic bracket 31 is made of a synthetic resin and has a reinforcing member 38 provided therein. The reinforcing member 38 has a bottom rear surface 39 exposed so as to form a part of a bracket base surface 36, but slightly recessed. (by dimension t1 in FIG. 3) from the bracket base surface 36.

Thus, since the reinforcing member 38 has a bottom rear surface 39 slightly recessed from the bracket base surface 36 which is opposite to the tooth 10, the adhesive is allowed to flow into the recessed portion. This interposes a hardened adhesive layer of a predetermined thickness which induces the bond destruction at the time of debonding (separation). Thus, the enamel of tooth may be prevented from being damaged, as well as the debonding (separation) strength may be predetermined. Further, the bottom rear surface 39 may compensate the adhesion strength in the same manner as the fourth embodiment and more consolidate and assure the adhesion strength of the orthodontic bracket 31 if necessary.

(Sixth Embodiment)

Figure 4:
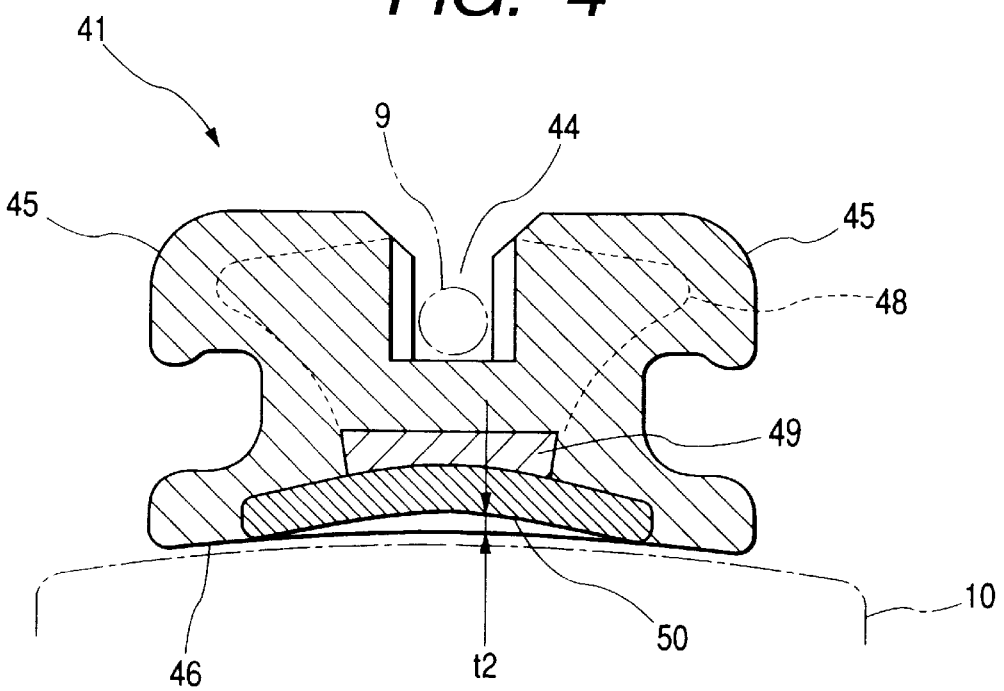
FIG. 4 is a diagrammatical view of a fifth embodiment of an orthodontic bracket according to the invention shown in vertical section.

The orthodontic bracket 41 according to the sixth embodiment as shown in FIG. 4 is formed in the same manner as the embodiment shown in FIG. 3. Namely, the orthodontic bracket 41 has one end surface fixed to the tooth 10 and has the opposite end side formed with a slot 44 extended between a pair of tie wings 45 for receiving the archwire 9 therein.

The orthodontic bracket 41 is, as is the preceding embodiments, made of a synthetic resin and has a reinforcing member 48 provided therein. The reinforcing member 48 has a bottom 49 having a bonding base member 50 fixed thereto. The bonding base member 50 is slightly bent to be recessed (by dimension t2 in FIG. 4) from a bracket base surface 46, and exposed so as to form a part of the bracket base surface 46.

Thus, since the reinforcing member 48 has the base member 50 fixed to the bottom 49 thereof and slightly recessed from the bracket base surface 46 and facing the tooth 10, the adhesive is allowed to flow into the recessed portion.

Further, the base member 50 may compensate the adhesion strength in the same manner as the fifth embodiment and more consolidate and assure the adhesion strength of the orthodontic bracket 41. This will further facilitate the debonding operation (separating operation).

Further, the base member 50 may be selected from proper material and may be properly processed to be attached to the reinforcing member 48 while the shape and surface property are variously determined.

Figure 5:
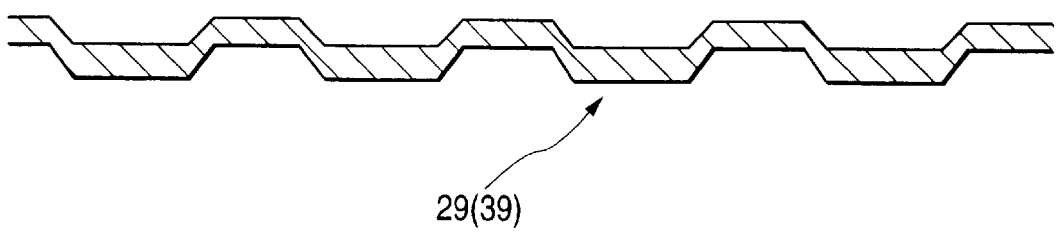
FIG. 5 is a diagrammatical view showing in section a bottom rear surface of a reinforcing member or a bottom surface of a base member incorporated in an orthodontic bracket according to the invention.
Figure 6:
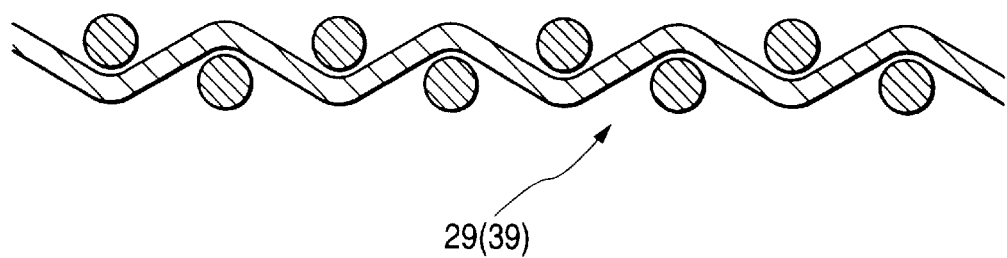
FIG. 6 is a diagrammatical view showing in section a bottom rear surface of a reinforcing member or a bottom surface of a base member incorporated in an orthodontic bracket according to the invention.

As to the fourth to sixth embodiments, it is preferable that the bottom rear surfaces 29, 39 of the reinforcing members 28, 38 and the base member 50 have a surface positioned opposite to the tooth 10. It is preferable that the surface is rugged as shown in FIG. 5 or being meshy as shown in FIG. 6. With such a surface shape as shown in FIGS. 5 or 6, the rugged dimensions and shapes may be variously changed to control the adhesion property.

Further, as to each of the orthodontic brackets according to the second to sixth embodiments, the synthetic resin may have glass filler contained therein. With this structure, the synthetic resin can be not only enhance its strength but also adjust its transparency.

In the orthodontic bracket of the invention thus structured, there will be no solvent crack due to the adhesive and much less hydrolysis because of lower water absorption while the durability is high in the mouth.

Further, the composite resin of PC/PET is excellent in fluidity at the time of molding and has little residual stress remained therein. Even if the residual stress remains at the time of molding, it is not sensitive to the solvent crack. Therefore, there is an advantage in production that the annealing which is otherwise required to eliminate the residual stress from PC may be skipped.

Further, since the surface of insufficient adhesion may be compensated by a part of the reinforcing member or by the metal bonding base, a sufficient adhesion strength can be obtained.

Additionally, if the material is polyether-sulfone, the strength for use in the mouth is excellent compared with PC and polysulfone.

Further, if the reinforcing member having the rugged or meshy surface is used, this is effective to increase the adhesion strength against the plastic member in addition to the bonding effect.

As to the color tone of the orthodontic bracket of the invention, since PC is used, the material is optimal for the plastic bracket of high aesthetic property because the material is characterized by non-crystalloid and transparency. On the other hand, the use of PC is problematical in deterioration of the resin due to solvent crack and hydrolysis. PET (a type of polyester), which is generally opaque crystal resin, may be alloyed with PC to be a translucent resin. Therefore, according to the invention, in case of, so called, a metal insert method wherein a metal reinforcing member is embedded within the bracket, the bracket may have a translucent or appropriate color to conceal the presence of reinforcing member.

The alloy of PC/PET in the market includes various grades, that is, substantially transparent, completely opaque, lower in transparency with glass filler added to increase the strength of bracket and the like, which may be optionally selected.

Further, PET includes a completely transparent amorphous one depending upon the grade as seen on PET bottles. The alloy of PET and PC may realize complete transparency, though the technical explanation is omitted herein. In this case, it is preferable to whiten the alloy. It is possible to cause the resin to have an inconspicuous translucent tone or a color like a tooth by, for example, mixing a minute amount of titanium oxide with the resin.

In the case where the orthodontic bracket of the present invention has the plastic base surface, the plastic base surface may be subjected to sandblast treatment to increase the adhesion strength by exposing the inorganic filler including glass filler or glass beads so as to be applied with silane coupling for adhesion.

According to the invention, a composite resin of PC/PET is used as a plastic material in the embodiments. However, polyether-sulfone (not a composite resin) may be used as a resin for bracket. In this case, the resin is better in durability than PC and polysulfone, and further the adhesion property is satisfactory.

The effects of the second to sixth embodiments can be confirmed by the following description of the results of tests and the comparison thereof concerning the orthodontic bracket according to the invention.

EXAMPLE 2

(1) Tests with Respect to Solvent Crack, Hydrolysis and Strength of Tie Wings

The orthodontic bracket as shown in FIGS. 1C and 1D was prepared, wherein the reinforcing member incorporated therein reaches the tie wings. As the composite resin, a polymer alloy of PC and PET was used to test the solvent crack and others.

The material is composed of two resins, that is, PC and PET in the ratio (wt %) of 7:3. The composite resin has a strength of the same degree as PC, excellent chemical resistance, relatively excellent transparency, and low water absorption.

First of all, the comparison tests of solvent crack were conducted.

Primer and monomer of 6 types of dental adhesives were applied to the resins such as PC/PET ("CALIBER CR-3341T produced by Sumitomo Dow Ltd.: polymer alloy of 70% of polycarbonate and 30% of polyethylene terephthalete), PC, polysulfone to confirm the degrees of solvent crack. The results are indicated in Table 3. In the Table, x mark indicates that the resin exhibited cracks at the time of application of primer and monomer, many of the cracks extending to the base and tie wings. PC and polysulfone exhibited the same degree of cracks. PC/PET exhibited no solvent crack which makes the resin practically useless.

TABLE 3

| Material Maker Trade name | Adhesive Name | | | | | | |
|---|---|---|---|---|---|---|---|
| | Super Bond (monomer) | Bracket Bond II (monomer) | Elan (primer) | Ideal (primer) | Fujiortho LC (primer) | Ortholock (primer) | Accubond (liquid) |
| PC/PET Sumitomo Dow CALIBER | o | o | Δ | Δ | o | Δ | o |
| Polycarbonate/ GE Plastic lexan | o | x | x | x | o | x | x |
| Polysulfone/ Amoco Udel | x | x | x | x | o | x | o | o: No change; Δ: Slightly change, but no problem for practical use; x: useless

Subsequently the comparative tests of adhesion strength were conducted.

As shown in Table 4, the orthodontic bracket using PC/PET according to the embodiments was subjected to sandblast treatment to increase the adhesion strength at the rear surface of base. It was found out that the PC/PET was the same degree as PC and polysulfone.

The resin of PET 100% was not adhered.

Incidentally, used bracket type is AN (Lower Anteriors), and the unit of shear bond strength is Kgf in Table 4.

TABLE 4

| Material Maker Trade name Condition | Adhesive Name | | | | | |
|---|---|---|---|---|---|---|
| | Super Bond | Elan | Ideal | Fujiortho LC | ortholock | Accubond |
| PC/PET/ Sumitomo Dow CR-3341T Sandblasted | 11.5 | 7.0 | 6.8 | — | 10–13 | 6.8 |
| Polycarbonate/ GE Plastic lexan containing 10% of filler | 15.0 | — | 7.5 | 9.0 | 10.6 | 7.5 |
| Polysulfone/ Amoco Udel Sandblasted | 17.4 | 14.7 | 13.9 | 9.4 | 10.5 | 9.6 |

As to the tie wings, tests were carried out as compared with PC.

The tie wings are needed to fix the archwire to the bracket by means of the ligature wire and the elastomeric ligature rings(ERL). It is generally known that the tie wings can be damaged, cracked or the slot can be deformed by the tying force depending upon the plastic material and the shape of reinforcing member positioned within the plastic.

The orthodontic bracket using PC/PET according to the embodiments was compared with 2 types of PC brackets produced by the applicant. As shown in Table 3, it was found out that the tie wings had a strength same as the conventional ones because the orthodontic bracket using PC/PET has the reinforcing member so formed as to extend into the tie wings.

TABLE 5

| | |
|---|---|
| PC/PET/Sumitomo Dow CR-3341T; No filler | 9.0–9.4 |
| Polycarbonate/GE Plastic lexan; No filler | 9.0 |
| Polycarbonate/Teijin Chemical Panlite; 10% filler | 13.0 or more |

(Unit: kgf)

EXAMPLE 3

(2)Tests with Respect to Adhesion Strength

As shown in FIGS. 2A and 2B, the metal reinforcing member according to the embodiment of the invention was so formed as to partly extend to reinforce the tie wings and had the bottom exposed to be a part of the bonding base surface. The bonding base surface of reinforcing member was, as one sample, in the same plane with the plastic portion as shown in FIG. 2A, and as another sample, was slightly recessed from the plastic portion as shown in FIG. 3. The tests were conducted under the same adhesion conditions compared with the conventional orthodontic bracket wherein the reinforcing member is not exposed.

As a result, the orthodontic bracket according to the present invention exhibited higher adhesion effects in any cases by use of metal increasing the adhesion strength when compared with the conventional one. Further, as shown in FIG. 4, the meshy bonding base member was welded to the bottom of the metal reinforcing member. In this case, the meshy structure increased the adhesion strength as well.

What is claimed is:

1. An orthodontic appliance that fits into the mouth as an orthodontic device, said appliance comprising one of an orthodontic bracket or an archwire comprising an element constructed by dispersing thermoplastic elastomer in a matrix resin.

2. The orthodontic appliance according to claim 1, wherein said matrix resin is a polycarbonate resin and said thermoplastic elastomer is styrene elastomer.

3. The orthodontic appliance according to claim 2, wherein a content of said styrene elastomer is 0.5 wt % to 10.0 wt %.

4. The orthodontic appliance according to claim 3, wherein the content of said styrene elastomer is 0.5 wt % to 2.0 wt %.

5. The orthodontic appliance according to claim 2, wherein a particle size of said styrene elastomer is 0.1 μm to 10 μm.

6. The orthodontic appliance according to claim 1, wherein said appliance is a bracket and wherein at least one reinforcing member is provided at a slot of said bracket, said reinforcing member exposed to an inner wall surface of the slot and reinforcing the inner wall surface.

7. The orthodontic appliance according to claim 6, wherein said reinforcing member is extended into tie wings which are formed as being extended towards the gingival side and occlusal side of the slot.

8. The orthodontic appliance according to claim 6, wherein said bracket has a hook and said reinforcing member has a hook core member provided to reinforce the hook of said bracket.

9. The orthodontic appliance according to claim 1, wherein said matrix resin contains an inorganic filler.

10. An orthodontic bracket having one end side surface adapted to be fixed to a tooth and having the opposite end side formed with a slot which is designed to be engaged by an arch wire; comprising a composite resin having a first synthetic resin for providing a strength of the orthodontic bracket in the mouth and a second synthetic resin for providing an adhesion property thereof.

11. The orthodontic bracket according to claim 10, wherein the first synthetic resin includes polyethylene-terephtalete and the second synthetic resin includes polycarbonate, said polycarbonate ranges 30 to 80 wt %.

12. The orthodontic bracket according to claim 10, further comprising a bonding base area for providing a surface to be adhered to a tooth and a bracket member area which is continuous to the bonding base area and is formed with the slot and tie wings;

wherein polycarbonate contained in the bonding base area is in the range of 60 to 100 wt %, and polyethylene-terephtalete contained in the bracket member area is 60 to 100 wt %.

13. An orthodontic bracket having one end side surface adapted to be fixed to a tooth and having the opposite end side formed with a slot which is designed to be engaged by an arch wire, comprising a reinforcing member provided in said bracket made of a synthetic resin so that a part of said reinforcing member is exposed at a base surface which is positioned opposite to the tooth.

14. The orthodontic bracket according to claim 13, wherein a rear surface of a bottom of said reinforcing member is slightly recessed from said base surface.

15. The orthodontic bracket according to claim 13, wherein said reinforcing member is extended into tie wings which are formed as being extended towards the gingival side and the occlusal side of said slot.

16. The orthodontic bracket according to claim 14, wherein said rear surface of said bottom of said reinforcing member or said base member has a surface facing the tooth, said surface being rugged or meshy.

17. The orthodontic bracket according to claim 1, wherein the synthetic resin is polyether-sulfone and styrene elastomer.

18. The orthodontic bracket according to claim 1, wherein the synthetic resin is a composite resin.

19. The orthodontic bracket according to claim 10, wherein the synthetic resin contains inorganic filler therein.

20. The orthodontic bracket according to claim 13, wherein the synthetic resin contains inorganic filler therein.

21. The orthodontic bracket of claim 13, wherein the part of the reinforcing member which is exposed is a base member fixed to the reinforcing member.

22. The orthodontic bracket of claim 21, wherein a rear surface of the base member is slightly recessed from the base surface.

* * * * *